United States Patent

Cottingham et al.

[11] 4,029,959
[45] June 14, 1977

[54] PLANT LIGHT SENSOR ADAPTOR

[75] Inventors: Hugh Cottingham, Upper Montclair; Joseph Scrocco, West Orange, both of N.J.

[73] Assignee: BHN, Inc., Upper Montclair, N.J.

[22] Filed: Feb. 13, 1976

[21] Appl. No.: 658,140

[52] U.S. Cl. .................................. 250/239; 250/215
[51] Int. Cl.² ........................ H01J 5/02; H01J 39/12
[58] Field of Search ............. 250/239, 226, 214 P; 324/4, 65 P, 65 R

[56] References Cited

UNITED STATES PATENTS

| | | | |
|---|---|---|---|
| 3,383,979 | 5/1968 | Gibson | 250/226 |
| 3,487,221 | 12/1969 | Frank | 250/239 |

*Primary Examiner*—Alfred E. Smith
*Assistant Examiner*—David K. Moore
*Attorney, Agent, or Firm*—Blum, Moscovitz, Friedman & Kaplan

[57] ABSTRACT

A plant light sensor adaptor for converting a plant soil moisture monitoring device into a plant light sensing device is provided. The plant soil moisture monitoring device includes first and second metal electrodes and an indicator coupled to the electrodes for sensing and indicating current flow due to the electro-galvanic response produced by the difference in the redox potential in the first and second metal electrodes, which current flow is controlled by the moisture content of the plant soil under test. The adaptor includes a reference member having a receiving portion for receiving the first and second metal electrodes, the receiving portion including first and second spaced apart electrically isolated contacts, the receiving portion being constructed and arranged to bring the first and second contacts respectively into electrical contact with the first and second metal electrode, and photosensitive circuitry coupled to the respective first and second spaced apart electrically isolated contacts, the photosensitive circuitry being adapted to detect the luminous flux incident thereon and in response thereto apply through the respective first contact and electrode, and through the respective second contact and electrode current signal representative of the luminous flux detected by the photo-sensitive circuitry, whereby the indicator senses and indicates the luminous flux detected by the photosensitive circuitry.

7 Claims, 4 Drawing Figures

U.S. Patent June 14, 1977 4,029,959
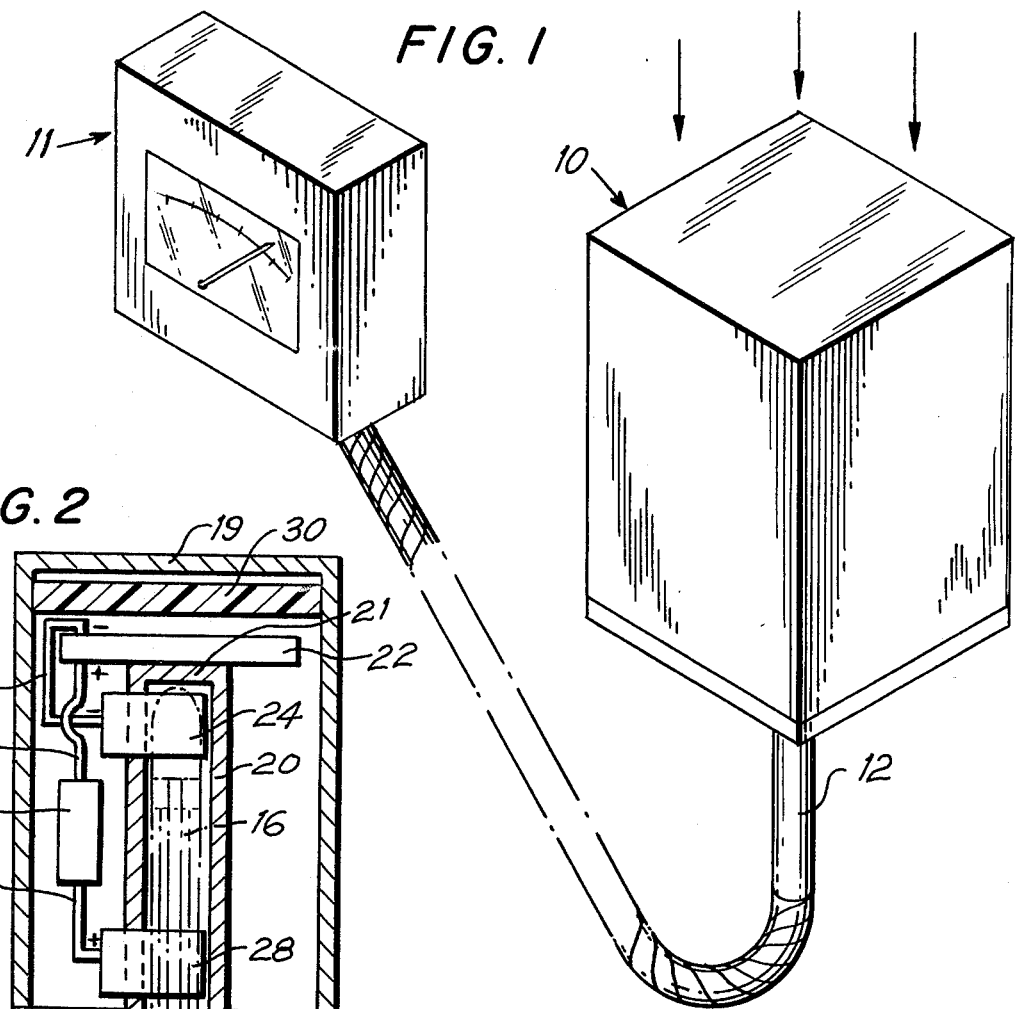
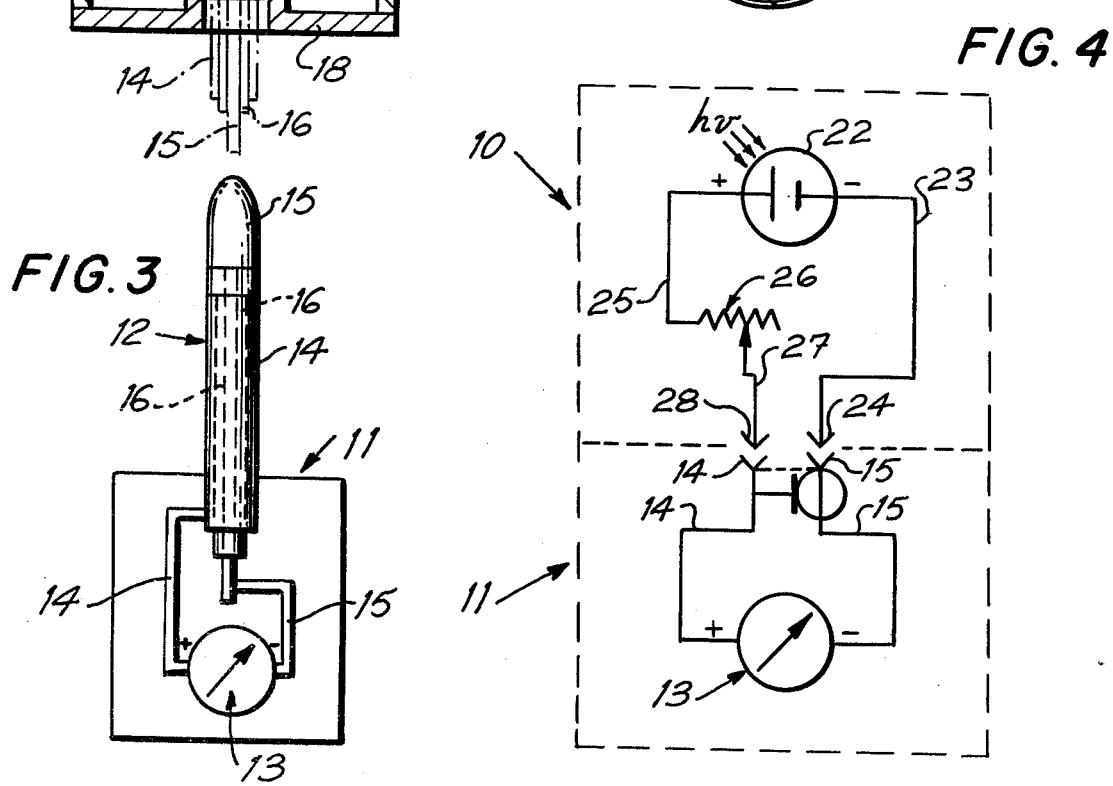

PLANT LIGHT SENSOR ADAPTOR

BACKGROUND OF THE INVENTION

This invention is directed to a plant light sensor adaptor for use with a plant soil moisture monitoring device, and in particular to a plant light sensor adaptor for converting a plant soil monitoring device including an indicator for sensing the amount of moisture in the plant soil to an indicator of luminous flux of the wavelengths in the visible light spectrum required for proper plant growth and substance.

Among the problems encountered by the home gardening enthusiast is the inability to effectively monitor the environmental factors critical to proper plant health and care. Among the environmental factors that are critical to most plant life is the moisture content of the plant soil and the luminous flux incident upon the plant.

While devices for measuring the moisture content of the plant soil have taken on various forms, one particularly simple type device is the use of an electro-galvanic response due to the difference in redox potentials of two dissimilar metal electrodes to effect a monitoring of the moisture content of the plant soil. Nevertheless, devices that have been provided for measuring the luminous flux incident upon the plant life have been less than completely satisfactory for use by the home plant enthusiast due to the complexity and cost of such light monitoring devices.

SUMMARY OF THE INVENTION

Generally speaking, in accordance with the invention, a plant light sensor adaptor for use with a plant soil moisture monitoring device is provided. The moisture monitoring device includes first and second metal electrodes and an indicator for sensing and indicating current flow due to the electro-galvanic response produced by the difference in the redox potential in the first and second metal electrodes, which current flow is controlled by the moisture content of the plant soil under test. The plant light sensor adaptor includes a reference member adapted to define a receiving portion for receiving the first and second metal detectors. The receiving portion includes first and second spaced apart electrically isolated contacts that are constructed and arranged to electricaly couple the first and second spaced apart contacts to the first and second metal electrodes, respectively, when the electrodes are received thereby. Photosensitive circuitry is coupled to the respective first and second spaced apart electrically isolated contacts. The photo-sensitive circuitry detects luminous flux and in response thereto applies through the respective first contact and electrode and the respective second contact and electrode a current signal representative of the luminous flux, whereby the indicator senses and indicates the luminous flux detected by the photo-sensitive circuitry.

Accordingly, it is an object of this invention to provide a inexpensive, simple yet effective plant light sensor adaptor.

A further object of this invention is to provide a plant light sensor adaptor for converting a plant soil moisture content monitoring device into a plant light sensing device.

Still a further object of the this invention is to provide an improved plant light sensor adaptor particularly adapted to sense the wavelengths in the visible light spectrum required for plant sustenance and growth.

Still other objects and advantages of the invention will in part be obvious and will in part be apparent from the specification and drawings.

The invention accordingly comprises the features of construction, combinations of elements, and arrangement of parts which will be exemplified in the constructions hereinafter set forth, and the scope of the invention will be indicated in the claims.

BRIEF DESCRIPTION OF THE DRAWINGS

For a fuller understanding of the invention, reference is had to the following description taken in connection with the accompanying drawings, in which:

FIG. 1 is a perspective view of a plant light sensor adaptor for use in combination with a plant soil moisture monitoring device and constructed in accordance with the instant invention;

FIG. 2 is a sectional view of the plant light sensor adaptor depicted in FIG. 1;

FIG. 3 is a part schematic, part elevational view of the plant soil moisture monitoring device depicted in FIG. 1; and FIG. 4 is a schematic illustration of the plant light sensor adaptor and plant soil moisture monitoring device illustrated in FIG. 1.

DETAILED DESCRIPTION OF THE PREFERRED EMBODIMENTS

Reference is now made to FIG. 1, wherein a plant light sensor adaptor, generally indicated as 10, is particularly suited for use with a plant soil moisture monitoring device generally indicated as 11. By way of background, reference is made to FIGS. 3 and 4 wherein a plant soil moisture monitoring device including a probe generally indicated as 12, and an ammeter generally indicated as 13 are depicted. The probe 12 includes a first positive coaxial electrode 14 coupled to the positive terminal of ammeter 13. Probe 12 further includes a second negative coaxial electrode 15 coupled to the negative terminal of the ammeter 13. The negative electrode 15 along the coaxial extent of the positive electrode is concentraically disposed with respect to the positive coaxial electrode 14 and is electrically isolated therefrom by an insulator 16. Additionally, the negative electrode forms the tip of the probe 12 and is also insulated from the portion of the positive electrode proximate thereto by insulator 16. The respective positive and negative electrodes are formed of dissimilar metals capable of producing a redox potential. The magnitude of the current produced by the redox potential is controlled by the moisture content of the plant soil in which the probe 12 is inserted. In a preferred embodiment, the negative tip electrode can be formed of magnesium and the positive electrode can be formed of chrome-plated brass so that the respective electrodes function like a battery to thereby generate EMF, which EMF produces a current flow through the ammeter 13 proportional to the degree of moisture. Ammeter 13 is sufficiently sensitive to minimum current and will provide full deflection with respect to current flow produced by the EMF generated across the respective electrodes to thereby provide an accurate representation of the moisture content of the plant soil.

It is noted that the plant soil moisture monitoring device device depicted in FIG. 3 provides an electro-galvanic response due to the difference in redox potential in the first and second metal detecting electrode which redox potential produces a current controlled by the moisture content of the plant soil under test. Nevertheless, the instant invention is not so limited and can be utilized with other plant soil moisture detecting devices of the type utilizing DC cells to energize the ammeter or current provided from a remote source.

Reference is now made to FIGS. 2 and 4, wherein the plant light sensor adaptor 10, constructed in accordance with the instant invention, is depicted. The adaptor 10 is formed of an integrally molded plastic support 18 and a plastic translucent cover 19. The support 18 is configured to define a cylindrical sleeve 20 dimensioned to receive the probe 12 of the moisture monitoring device 11. Additionally, the cylindrical sleeve 20 terminates in a top wall 21, which top wall is particularly suited for supporting a photo-sensitive cell 22 capable of producing an output voltage in response to the luminous flux detected thereby. In a preferred embodiment, a 0.5 V DC-MAX photo-sensitive cell is utilized to deliver approximately 200 $\mu$A at a maximum light condition and 0.0 $\mu$A in the absence of any light being incident upon the photo-sensitive cell. The negative terminal of the photo-sensitive cell is coupled through lead 23 to a resilient metal sheath contact 24, which contact is hereinafter referred to as the "negative contact". The positive terminal of the photo-sensitive cell is coupled through lead 25, variable calibrating resistor 26 and lead 27 to a resilient metal sheath contact 28, which contact is hereinafter referred to as the "positive contact". In a preferred embodiment, the variable calibrating resistor is a 5 K ohm variable resistor and as is detailed below, can be replaced with a fixed resistor once calibration is effected. The negative contact 24 and positive contact 28 are fixedly positioned by the sleeve 20 in longitudinally spaced apart relationship to thereby place same in registry with the negative coaxial electrode 15 and positive coaxial electrode 14, respectively, when the plant soil moisture monitoring device probe 12 is inserted into sleeve 20.

The plastic translucent cover 10 functions as a lens for directing the light incident upon the photosensitive cell and as an enclosure for the plant light sensor adaptor by being releasably securable to the support 18 in a conventional manner. It is noted that it is only necessary for the surface proximate to the photosensitive cell to be translucent but when actual manufacturing techniques are considered, the provision of an integrally molded cover of translucent material efficiently combines the lens and enclosure features in a single element. The cover is also formed to fixedly position a color correcting filter 30 between the light sensitive surface of the photosensitive cell and the translucent cover to thereby insure that the photo-sensitive cell 22 is detecting only those wavelengths in the visible light spectrum required for plant growth, such as red and blue light.

In operation, the probe 12 of the plant soil moisture monitoring device 11 is inserted into the cylindrical sleeve 20 formed by the support 18. When the probe is fully inserted into the cylindrical sleeve, the negative contact 24 is brought into electrical contact with the negative coaxial electrode 15 and hence is electrically coupled to the negative terminal of ammeter 13. Similarly, the positive contact 28 is thereby coupled through the positive coaxial electrode 16 to the positive terminal of the ammeter 13, thereby coupling the positive electrode of the photosensitive cell 22 to the positive terminal of the ammeter. By utilizing the variable calibrating resistance 26, the ammeter can be adjusted to provide zero deflection in response to no light being detected by the photo-sensitive cell 22 and can provide full deflection when the maximum amount of light is detected by the photosensitive cell 22. Once calibration is effect with respect to the particular ammeter utilized thereafter the variable calibrating resistance can be replaced by a fixed resistor. Accordingly, the ammeter 13 utilized to detect current flow produced by a difference in the positive and negative coaxial metal electrode potential is utilized to detect the luminous flux incident upon the photosensitive cell without the effectiveness of same as a moisture detecting meter being diminished.

Accordingly, a simple, inexpensive, yet extremely sensitive plant light sensor adapted for use with well-known types of plant soil moisture monitoring devices is provided in accordance with the instant invention.

It will thus be seen that the objects set forth above, among those made apparent from the preceding description, are efficiently attained and, since certain changes may be made in the above construction without departing from the spirit and scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. A plant light sensor adaptor for use with moisture monitoring means having a coaxially formed probe including first and second metal eletrode means, and indicating means for sensing and indicating current flow due to electro-galvanic response produced by the difference in the redox potential in the first and second metal electrode means, said current flow being controlled by the moisture content of the substrate material under test, comprising in combination, a reference member including receiving means for receiving said probe, said receiving means including first and second spaced apart electrically isolated contact means, said receiving means being configured to dispose said probe at a predetermined position to dispose said first and second contact means in electrical contact with said first and second metal electrode means when said probe is inserted into said receiving means, and photosensitive means coupled to said respective first and second spaced apart electrically isolated contact means, said photosensitive means being adapted to detect the luminous flux incident thereon, and in response thereto apply through said respective first contact and metal electrode means and through said respective second contact and metal electrode means a current signal representative of the luminous flux whereby said indicating means senses and indicates the luminous flux detected by the photosensitive means.

2. A plant light sensor adaptor as claimed in claim 1, and including variable resistance means disposed intermediate one of said contact means and said photo-sensitive means.

3. A plant light sensor adaptor as claimed in claim 1, and including translucent cover means fixedly secured to said reference means for enclosing said adaptor and permitting light to be incident upon said photo-sensitive means.

4. A plant light sensor adaptor as claimed in claim 3, and including color correcting filter means positionally disposed by said cover means intermediate said cover means and said photosensitive means for filtering selected light spectra.

5. A plant light sensor adaptor as claimed in claim 1, wherein each of said contact means is a metal sheath contact.

6. A plant light sensor adaptor as claimed in claim 5, wherein said reference member receiving means defined an elongated receptacle configured to receive a like configured coaxial probe supporting said first and second electrodes.

7. A plant light sensor adaptor as claimed in claim 6, wherein said elongated receptacle positions said sheath contacts in spaced apart relationship along the lengthwise extent of said receptacle.

* * * * *